(12) United States Patent
Yahata et al.

(10) Patent No.: US 11,739,006 B2
(45) Date of Patent: Aug. 29, 2023

(54) WATER QUALITY MEASUREMENT DEVICE AND WATER QUALITY MEASUREMENT METHOD

(71) Applicant: Shimadzu Corporation, Kyoto (JP)

(72) Inventors: Masahito Yahata, Kyoto (JP); Yuichi Masuda, Kyoto (JP); Tatsuya Kataoka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 507 days.

(21) Appl. No.: 16/624,091

(22) PCT Filed: Jun. 20, 2018

(86) PCT No.: PCT/JP2018/023454
§ 371 (c)(1),
(2) Date: Dec. 18, 2019

(87) PCT Pub. No.: WO2018/235865
PCT Pub. Date: Dec. 27, 2018

(65) Prior Publication Data
US 2020/0207643 A1    Jul. 2, 2020

(30) Foreign Application Priority Data
Jun. 21, 2017    (JP) ................. 2017-121325

(51) Int. Cl.
*C02F 1/32* (2023.01)
*C02F 1/72* (2023.01)
(Continued)

(52) U.S. Cl.
CPC ............... *C02F 1/325* (2013.01); *C02F 1/72* (2013.01); *G01N 27/06* (2013.01);
(Continued)

(58) Field of Classification Search
None
See application file for complete search history.

(56) References Cited

U.S. PATENT DOCUMENTS

| 4,868,127 A | 9/1989 | Blades et al. |
| 6,299,844 B1 | 10/2001 | Tao et al. |

(Continued)

FOREIGN PATENT DOCUMENTS

| DE | 19507189 A1 | 9/1996 |
| JP | H10-307114 A | 11/1998 |

(Continued)

OTHER PUBLICATIONS

Written Opinion of the International Search Authority for PCT/JP2018/023454 (dated Sep. 18, 2018), submitted with a machine translation (partial).

(Continued)

*Primary Examiner* — Richard C Gurtowski
(74) *Attorney, Agent, or Firm* — Muir Patent Law, PLLC (57) ABSTRACT

A water quality measurement device 1 includes a twin tube excimer lamp 2. The inflow pipe 3 is connected to one end of the inner tube 21 of the excimer lamp 2, and the outflow pipe 4 is connected to the other end of the inner tube 21 of the excimer lamp 2. The detector 5 that measures the conductivity of sample water is interposed in the outflow pipe 4. In the water quality measurement device 1, sample water sequentially flows through the inflow pipe 3, the inner tube 21 of the excimer lamp 2, and the outflow pipe 4. Hence, the channel in the water quality measurement device 1 can be simplified. Additionally, the sample water is oxidized by being irradiated with UV light in the inner tube 21 of the excimer lamp 2. Hence, it is possible to irradiate the sample water with UV light from the excimer lamp 2 efficiently.

9 Claims, 9 Drawing Sheets

(51) Int. Cl.
*G01N 27/06* (2006.01)
*G01N 33/18* (2006.01)

(52) U.S. Cl.
CPC .... *G01N 33/1846* (2013.01); *C02F 2201/322* (2013.01); *C02F 2201/326* (2013.01); *C02F 2209/40* (2013.01)

(56) References Cited

U.S. PATENT DOCUMENTS

| | | | |
|---|---|---|---|
| 6,737,276 | B1 | 5/2004 | Voss et al. |
| 8,729,500 | B2 | 5/2014 | Mastenbroek et al. |
| 2006/0108910 | A1 | 5/2006 | Justel et al. |
| 2009/0246882 | A1 | 10/2009 | Pochy et al. |
| 2012/0012537 | A1* | 1/2012 | DeCoster ............... C02F 1/325 250/435 |
| 2013/0134104 | A1* | 5/2013 | Forstmeier ............... C02F 1/76 210/756 |
| 2015/0035429 | A1* | 2/2015 | Hishinuma ............ C02F 1/325 313/631 |

FOREIGN PATENT DOCUMENTS

| JP | 2000-334295 A | 12/2000 |
|---|---|---|
| JP | 3268447 A | 1/2002 |
| JP | 2003-211159 A | 7/2003 |
| JP | 2005-536843 A | 12/2005 |
| JP | 2006-87988 A | 4/2006 |
| JP | 2010-56008 A | 3/2010 |
| JP | 2013-544016 A | 12/2013 |
| JP | 2014-213244 A | 11/2014 |

OTHER PUBLICATIONS

Oppenlander et al., "Photochemical Treatment of Water: Comparison of Incoherent Excimer Lamps with a Medium-Pressure Mercuy Lamp", Chem Eng. Technology vol. 21 No. 6, pp. 502-505, Jan. 29, 1999.
Oppenlander et al., "Photochemische Wasserbehandlung mit einem KrCl*-Excimer-UV-Rundrohrstrahler in einem Flachbettreaktor", Chemie Ingenieur Technik vol. 69, No. 10, pp. 1470-1474, Oct. 1, 1997, submitted with a machine translation.
European Search Report for corresponding patent application EP 18 82 0500, dated Jun. 3, 2020.
Office Action from the Chinese Intellectual Property Office for corresponding application No. 201880041669.1 dated Oct. 26, 2019.
Office Action dated Jul. 20, 2022 from the Chinese Intellectual Property Office for corresponding application No. 201880041669.1.
Decision of Final Rejection dated Jan. 20, 2023 from the Chinese Intellectual Property Office for corresponding application CN 201880041669.1.

* cited by examiner

WATER QUALITY MEASUREMENT DEVICE AND WATER QUALITY MEASUREMENT METHOD

TECHNICAL FIELD

The present invention relates to a water quality measurement device and a water quality measurement method for measuring the quality of sample water.

BACKGROUND ART

One method of oxidizing sample water in a water quality measurement device is a so-called wet oxidation method in which sample water is oxidized by using UV radiation. The wet oxidation method is mainly used when pure water or the like is the measurement target (see Patent Document 1 below, for example).

In the device described in Patent Document 1, sample water is fed into a reaction chamber, whereby the sample water is introduced around a UV lamp. Then, the sample water is oxidized by irradiation with UV light from the UV lamp.

As a device for implementing such a wet oxidation method, a device using an excimer lamp or a mercury lamp as a light source has been proposed, for example. When an excimer lamp is used as the light source, UV light having a high energy density can be irradiated (see Patent Documents 2 and 3 below, for example).

In a device described in Patent Document 2, a channel is formed so as to surround the periphery (outside) of an excimer lamp. Then, sample water is oxidized by UV light irradiated from the excimer lamp in the process of passing through the channel.

Additionally, in a device described in Patent Document 3, a channel is formed so as to penetrate the inside of a cylindrical lamp. Then, sample water is oxidized by UV light irradiated from the lamp in the process of passing through the channel.

PRIOR ART DOCUMENTS

Patent Documents

Patent Document 1: U.S. Pat. No. 6,737,276
Patent Document 2: JP 2014-213244 A
Patent Document 3: JP 3268447 B2

SUMMARY OF THE INVENTION

Problems to be Solved by the Invention

In the devices described in Patent Documents 1 and 2, the light source is located inside, and the sample water is located outside the light source. The UV light traveling toward the sample water from the light source diffuses so as to spread outward. For this reason, there has been a problem that the irradiation efficiency of UV light is lowered. Moreover, since the channel is provided around the light source, there has been a problem that the configuration of the channel becomes complicated.

Additionally, in the device described in Patent Document 3, a channel tube different from the lamp is inserted into the lamp. Hence, there has been a problem that the configuration becomes complicated. There has also been a problem that a gap is formed between the channel tube and the lamp, and the irradiation efficiency of UV light is lowered.

The present invention has been made in view of the above circumstances, and aims to provide a water quality measurement device and a water quality measurement method that can simplify the configuration of a channel of sample water, and can improve the irradiation efficiency of UV light on sample water.

Means for Solving the Problems (1) A water quality measurement device according to the present invention includes a UV light irradiation portion, an inflow pipe, an outflow pipe, and a detector. The UV light irradiation portion has a passage region through which sample water passes, and irradiates the sample water with UV light from around the passage region. The inflow pipe is arranged to allow sample water to flow into the passage region. The outflow pipe is arranged to allow the sample water oxidized by being irradiated with UV light by the UV light irradiation portion to flow out of the passage region. The detector detects the degradation product that has flowed into the outflow pipe.

According to such a configuration, the sample water sequentially flows through the inflow pipe, the passage region of the UV light irradiation portion, and the outflow pipe.

Hence, the channel in the water quality measurement device can be simplified.

Additionally, the sample water in the passage region is oxidized by the UV light irradiated inward from the periphery of the passage region.

Hence, it is possible to irradiate the sample water with UV light from the excimer lamp efficiently.

That is, according to the water quality measurement device of the present invention, the channel of sample water can be simplified, and the irradiation efficiency of UV light on sample water can be improved.

(2) In addition, the UV light irradiation portion may be a twin tube excimer lamp that has an inner tube in which an internal space is formed as the passage region and an outer tube disposed around the inner tube, and emits UV light by generating a discharge between electrodes provided on an inner peripheral surface of the inner tube and an outer peripheral surface of the outer tube. The inflow pipe may be arranged to allow sample water to flow into the inner tube from one end. The outflow pipe may be arranged to allow the sample water oxidized by being irradiated with UV light in the inner tube to flow out from the other end of the inner tube.

According to such a configuration, the sample water sequentially flows through the inflow pipe, the inner tube of the excimer lamp, and the outflow pipe.

Hence, the channel in the water quality measurement device can be simplified.

Additionally, the sample water is oxidized by being irradiated with UV light in the inner tube of the excimer lamp. Further, the illuminance of the excimer lamp stabilizes in a shorter time as compared with a mercury lamp or the like.

Hence, it is possible to irradiate the sample water with UV light from the excimer lamp efficiently in a short time.

Furthermore, since the inner tube itself of the lamp is directly used as a channel, the distance from the light emission position to the sample water can be shortened, and the irradiation efficiency of UV light on sample water can be improved.

That is, according to the water quality measurement device of the present invention, the channel of sample water can be simplified, and the irradiation efficiency of UV light on sample water can be improved.

(3) Additionally, the detector may detect the degradation product by measuring conductivity of the sample water that has flowed into the outflow pipe.

According to such a configuration, the degradation product can be detected accurately by measuring the conductivity of sample water.

(4) Additionally, the outflow pipe may include a heat dissipation portion. The heat dissipation portion dissipates the heat of sample water.

According to such a configuration, the heat dissipation portion can dissipate the heat of the oxidized sample water. Then, the degradation product can be detected by the detector with the temperature of the sample water brought close to the ambient temperature.

(5) Additionally, the excimer lamp may include a shielding portion. The shielding portion covers an outer peripheral surface of the outer tube and prevents UV light from leaking to the outside.

According to such a configuration, it is possible to prevent UV light from leaking to the outside with a simple configuration in which the outer tube is covered with the shielding portion and other structures are not provided, and it is therefore possible to improve the irradiation efficiency of UV light on sample water.

(6) Additionally, a reflecting surface that reflects UV light may be formed on an inner surface of the shielding portion.

According to such a configuration, the UV light emitted from the excimer lamp and traveling toward the outside can be reflected by the reflecting surface provided in the shielding portion, and be directed toward the inside of the excimer lamp. Then, sample water can be oxidized by being irradiated with UV light reflected and traveling toward the inside of the excimer lamp.

Hence, the irradiation efficiency of UV light on sample water can be improved even more.

(7) Additionally, a fluorescent agent may be applied to an inner surface of the shielding portion.

According to such a configuration, when the UV light from the excimer lamp hits the inner surface of the shielding portion, light (fluorescence) having a wavelength different from the wavelength of the UV light emitted from the excimer lamp is emitted by the fluorescent agent.

Accordingly, light having a wavelength different from the wavelength of UV light emitted from the excimer lamp can be irradiated toward the sample water.

(8) Additionally, the water quality measurement device may further include a liquid feed controller. The liquid feed controller is arranged to allow sample water to flow into the inner tube from the inflow pipe, irradiates the sample water in the inner tube with UV light by the excimer lamp with the inflow of sample water stopped, and resumes the inflow of sample water into the inner tube from the inflow pipe to send the oxidized sample water to the detector through the outflow pipe.

According to such a configuration, by repeatedly allowing inflow of sample water into the inner tube of the excimer lamp and stopping the inflow, it is possible to repeat the operation of oxidizing sample water by UV light from the excimer lamp and detecting the oxidized sample water by the detector.

Hence, the operation of oxidizing sample water and detecting the oxidized sample water by the detector can be performed according to simple control.

In particular, the illuminance of the excimer lamp stabilizes in a short time. Hence, sample water can be detected repeatedly in a short time.

(9) Additionally, a water quality measurement method according to the present invention includes an inflow step, an irradiation step, an outflow step, and a detection step. In the inflow step, sample water is allowed to flow, through an inflow pipe, into a passage region of a UV light irradiation portion that has the passage region through which sample water passes and irradiates the sample water with UV light from around the passage region. In the irradiation step, the sample water in the passage region is irradiated with UV light by the UV light irradiation portion. In the outflow step, the sample water oxidized by being irradiated with UV light by the UV light irradiation portion is allowed to flow into an outflow pipe from the passage region. In the detection step, a degradation product that has flowed into the outflow pipe is detected.

(10) Additionally, in the inflow step, sample water may be allowed to flow, through the inflow pipe, from one end into an inner tube of a twin tube excimer lamp that has the inner tube in which an internal space is formed as the passage region and an outer tube disposed around the inner tube, and emits UV light by generating a discharge between electrodes provided on an inner peripheral surface of the inner tube and an outer peripheral surface of the outer tube. In the irradiation step, the sample water in the inner tube may be irradiated with UV light by the excimer lamp. In the outflow step, the sample water oxidized by being irradiated with UV light in the inner tube may be allowed to flow into the outflow pipe from the other end of the inner tube.

(11) Additionally, in the detection step, the degradation product may be detected by measuring conductivity of the sample water that has flowed into the outflow pipe.

(12) Additionally, the water quality measurement method may further include a heat dissipation step. In the heat dissipation step, heat of the sample water that has flowed into the outflow pipe is dissipated.

(13) Additionally, in the irradiation step, the sample water in the inner tube may be irradiated with UV light by the excimer lamp with the inflow of sample water into the inner tube from the inflow pipe stopped. In the outflow step, the inflow of sample water into the inner tube from the inflow pipe may be resumed to send the oxidized sample water to the detector through the outflow pipe.

Effects of the Invention

According to the present invention, the sample water sequentially flows through the inflow pipe, the inner tube of the excimer lamp, and the outflow pipe. Hence, the channel in the water quality measurement device can be simplified. Additionally, the sample water is oxidized by being irradiated with UV light in the inner tube of the excimer lamp. Hence, it is possible to irradiate the sample water with UV light from the excimer lamp efficiently.

MODE FOR CARRYING OUT THE INVENTION

1. Overall Configuration of Water Quality Measurement Device

Figure 1:
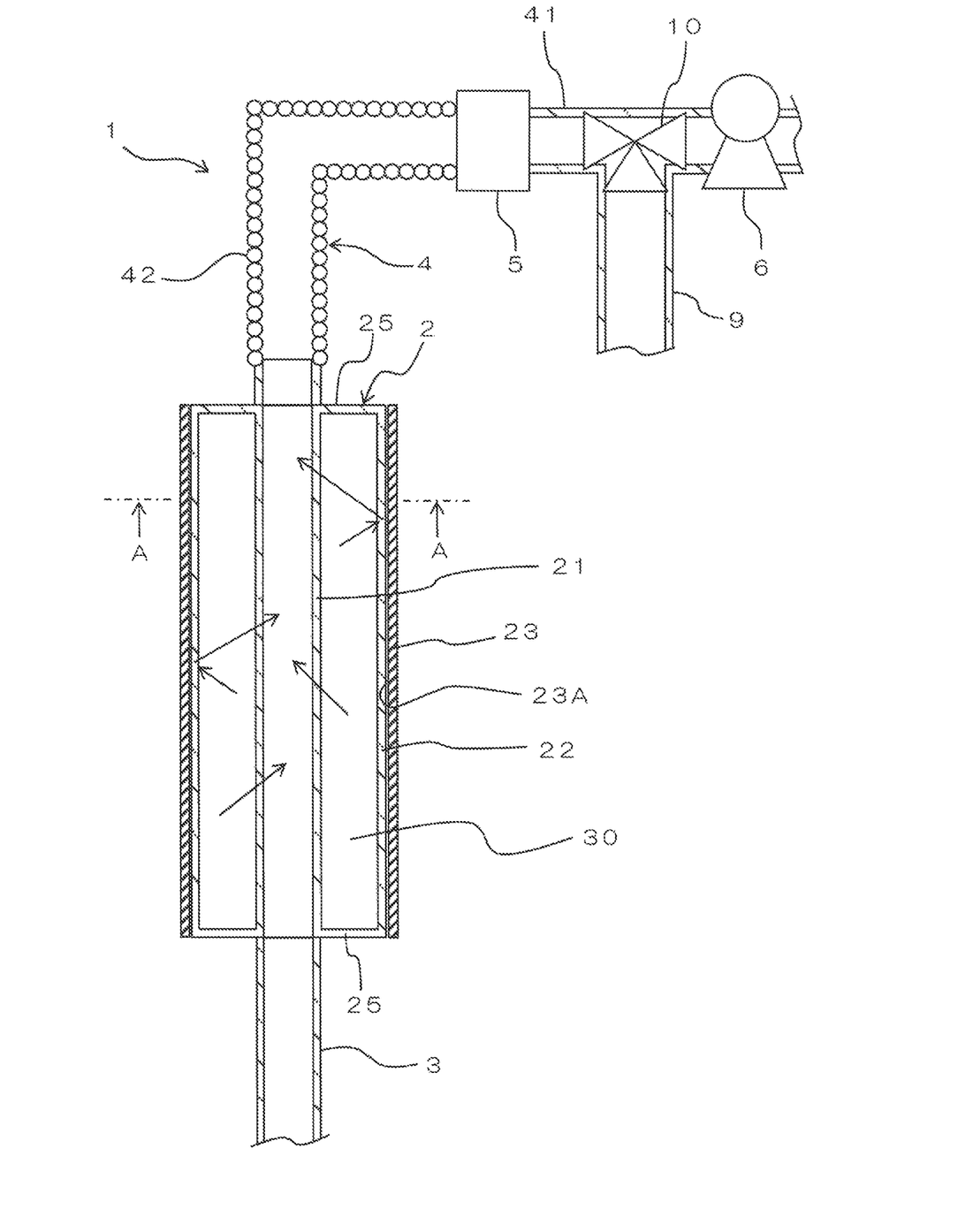
FIG. 1 is a schematic diagram showing a configuration of a water quality measurement device according to a first embodiment of the present invention.

FIG. 1 is a schematic diagram showing a configuration of a water quality measurement device 1 according to a first embodiment of the present invention.

The water quality measurement device 1 is a device for measuring the concentration of total organic carbon (TOC) in sample water, and is a so-called wet oxidation measurement device that oxidizes organic matter in sample water by irradiating the sample water with UV light. The water quality measurement device 1 detects the degradation product (oxidative degradation product) of sample water by measuring the conductivity of the sample water. The water quality measurement device 1 includes an excimer lamp 2, an inflow pipe 3, an outflow pipe 4, a detector 5, a pump 6, a bypass pipe 9, and a three-way valve 10.

Figure 2:
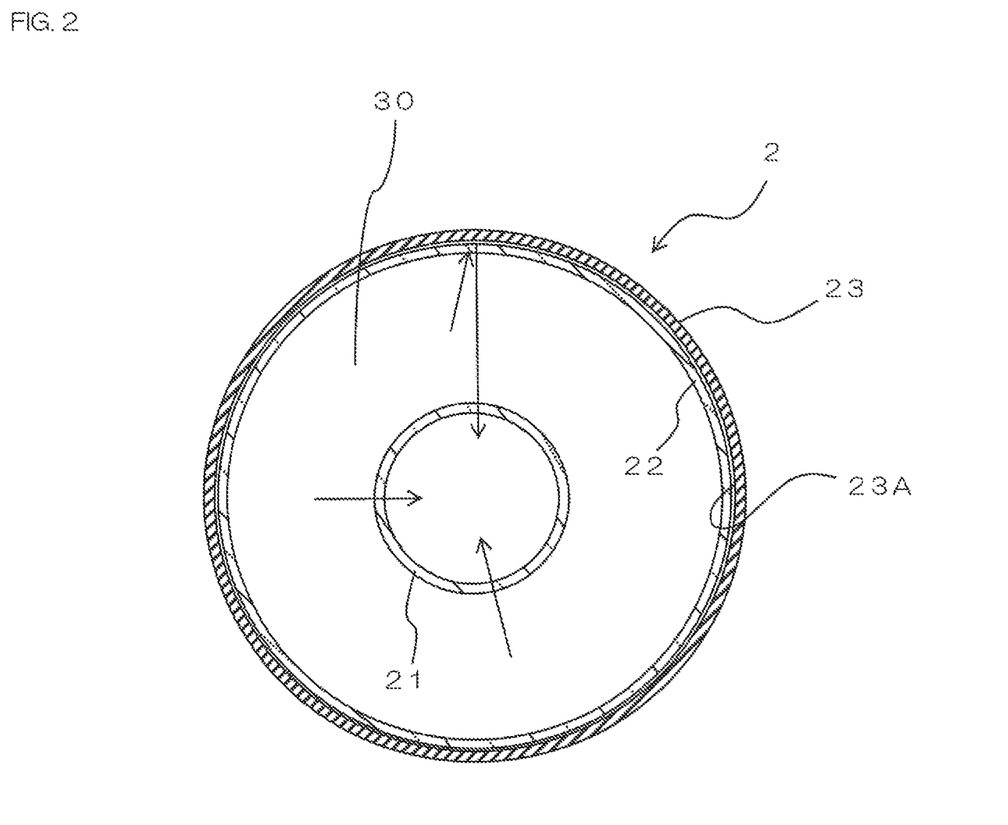
FIG. 2 is a cross-sectional view taken along line A-A of an excimer lamp of FIG. 1.

FIG. 2 is a cross-sectional view taken along the line A-A of the excimer lamp 2 of FIG. 1.

As shown in FIGS. 1 and 2, the excimer lamp 2 is a twin tube excimer lamp, and includes an inner tube 21, an outer tube 22, and a shielding portion 23. The excimer lamp 2 forms an example of a UV light irradiation portion. Specifically, in this example, the excimer lamp 2 is a twin cylinder excimer lamp. The excimer lamp 2 does not necessarily have to be a twin cylinder type, and only needs to be a twin tube type. Note that the twin cylinder excimer lamp 2 as used in the embodiment has a more preferable configuration because it has high compatibility with piping and material procurement is easy.

The inner tube 21 is made of a glass material and is formed in a long cylindrical shape. Although not shown, an electrode is provided on an inner peripheral surface of the inner tube 21. The inner diameter of the inner tube 21 is 0.5 mm to 2.0 mm, for example. An internal space of the inner tube 21 is formed as a channel through which sample water passes. The capacity of the inner tube 21 is 0.05 ml to 0.40 ml, for example. The internal space of the inner tube 21 forms an example of a passage region.

The outer tube 22 is disposed outside the inner tube 21 so as to surround the inner tube 21 with a space interposed therebetween. The outer tube 22 is made of a glass material and is formed in a long cylindrical shape. The central axis of the outer tube 22 coincides with the central axis of the inner tube 21. Although not shown, an electrode is provided on an outer peripheral surface of the outer tube. The longitudinal dimension of the outer tube 22 and the inner tube 21 is 3 cm to 30 cm, and preferably about 10 cm, for example. One end of the outer tube 22 and one end of the inner tube 21 are connected by an end surface 25. Similarly, the other end of the outer tube 22 and the other end of the inner tube 21 are connected by an end surface 25. With such a configuration, an annular discharge space 30 defined by the inner tube 21, the outer tube 22, and the end surfaces 25 is formed in the excimer lamp 2. A gas for discharge (discharge gas) is enclosed in the discharge space 30. In the example, xenon (Xe) is enclosed in the discharge space 30 as the discharge gas.

The shielding portion 23 is provided on the outer peripheral surface of the outer tube 22. The shielding portion 23 covers the entire outer peripheral surface of the outer tube 22. The shielding portion 23 is made of aluminum foil, for example. An inner surface 23A (surface facing outer tube 22) of the shielding portion 23 functions as a reflecting surface that reflects UV light.

With such a configuration, in the excimer lamp 2, when voltage is applied to the electrode provided in the inner tube 21 and the electrode provided in the outer tube 22, a discharge is generated in the discharge space 30. This discharge excites the discharge gas in the discharge space 30 and creates an excimer state. Then, light emission occurs when the excimer state returns to the original state (normal state). Of the light (UV light), light traveling radially inward flows into the inner tube 21, and light traveling radially outward is reflected by the inner surface 23A of the shielding portion 23 to travel radially inward, and flows into the inner tube 21. That is, of the light generated in the discharge space 30, light traveling toward the outside of the outer tube 22 is shielded by the shielding portion 23, and reflected by the inner surface 23A of the shielding portion 23 to travel radially inward. Accordingly, the light in the discharge space 30 is prevented from leaking from the outer tube 22 to the outside by the shielding portion 23, and the light in the discharge space 30 efficiently flows into the inner tube 21.

Note that in the water quality measurement device 1, light (UV light) having a high energy density around 172 nm (172 nm to 180 nm) is generated. Hence, when sample water is oxidized in the water quality measurement device 1, the sample water can be oxidized in a short time.

The inflow pipe 3 is connected to one end (lower end in FIG. 1) of the inner tube 21 of the excimer lamp 2. The inner diameter of the inflow pipe 3 is substantially the same as the inner diameter of the inner tube 21 of the excimer lamp 2. Note that of the ends of the inner tube 21, the one end of the inner tube 21 is the end of the inner tube 21 located on the upstream side of the inflow direction of sample water.

The outflow pipe 4 is connected to the other end (upper end in FIG. 1) of the inner tube 21 of the excimer lamp 2. The outflow pipe 4 includes a pipe main body 41 and a heat dissipation portion 42.

The pipe main body 41 is formed in a long pipe shape. The pipe main body 41 is connected to the other end of the inner tube 21 of the excimer lamp 2. The inner diameter of the pipe main body 41 is substantially the same as the inner diameter of the inner tube 21 of the excimer lamp 2. Note that of the ends of the inner tube 21, the other end of the inner tube 21 is the end of the inner tube 21 located on the downstream side of the inflow direction of sample water.

The heat dissipation portion 42 is configured to dissipate the heat of sample water, and is interposed in an intermediate part of the pipe main body 41. The heat dissipation portion 42 is a heat dissipating coil formed in a pipe shape (tubular shape). Specifically, the heat dissipation portion 42 is formed in a pipe shape (tubular shape) by winding a metal wire having a length of 500 mm to 2000 mm. The heat dissipation portion 42 dissipates (heat-dissipates) the heat of the oxidized sample, and stabilizes the temperature of the sample water flowing into the detector 5. Note that the outflow pipe 4 is not limited to the configuration in which a part of the outflow pipe 4 is the heat dissipation portion 42, and the entire outflow pipe 4 may be formed of the heat dissipation portion 42.

The detector 5 is interposed in an intermediate part of the outflow pipe 4 (pipe main body 41). Specifically, the detector 5 is located downstream of the heat dissipation portion 42 in the inflow direction of sample water. The sample water that has passed through the heat dissipation portion 42 flows into the detector 5. The detector 5 is a conductivity detector that measures the conductivity of liquid, and measures the conductivity of sample water in the outflow pipe 4.

The pump 6 is disposed in an intermediate part of the outflow pipe 4 (pipe main body 41) downstream of the detector 5 in the inflow direction of sample water.

The bypass pipe 9 is connected to an intermediate part of the outflow pipe 4 (pipe main body 41) between the detector 5 and the pump 6.

The three-way valve 10 is provided at a connection part (merging part) between the outflow pipe 4 (pipe main body 41) and the bypass pipe 9. The three-way valve 10 performs a switching operation for switching the channel through which sample water flows. Specifically, the three-way valve 10 switches between a channel passing through the outflow pipe 4 from the detector 5 to the pump 6 and a channel passing through the bypass pipe 9 after passing through the outflow pipe 4.

In the water quality measurement device 1, sample water sequentially moves through the inflow pipe 3, the inner tube 21 of the excimer lamp 2, and the outflow pipe 4 by an operation of the pump 6. As will be described later, the water quality measurement device 1 appropriately moves and stops the sample water by controlling ON and OFF of the pump 6. Further, when the excimer lamp 2 is operated, sample water located in the inner tube 21 of the excimer lamp 2 is irradiated with light (UV light). The flow rate of sample water flowing into the inner tube 21 of the excimer lamp 2 is 1 to 30 ml/min, for example.

Then, as will be described later, in the water quality measurement device 1, the operation of the excimer lamp 2 as well as the pump 6 is controlled, so that the sample water before oxidation and the sample water after oxidation selectively flow into the outflow pipe 4. In the water quality measurement device 1, the detector 5 measures the conductivity of the sample water, and the concentration of total organic carbon (TOC) in the sample water is measured on the basis of the measurement result. Note that in this example, pure water is used as the sample water, for example.

2. Electrical Configuration of Controller and its Peripheral Members

Figure 3:
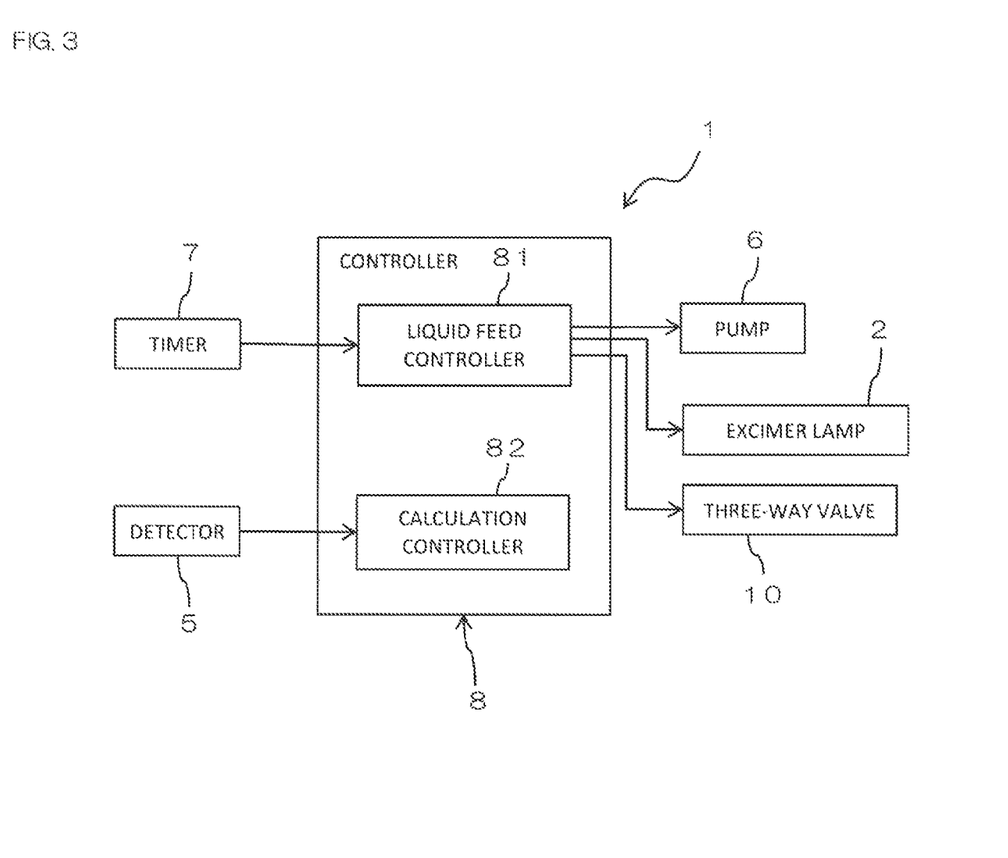
FIG. 3 is a block diagram showing an electrical configuration of a controller and its peripheral members.

FIG. 3 is a block diagram showing an electrical configuration of a controller and its peripheral members.

The water quality measurement device 1 includes a timer 7 and a controller 8 in addition to the excimer lamp 2, the detector 5, the pump 6, and the three-way valve 10 described above.

The timer 7 is configured to measure the elapsed time during operation of the water quality measurement device 1.

The controller 8 includes a central processing unit (CPU), for example, and parts such as the excimer lamp 2, the detector 5, the pump 6, and the timer 7 are electrically connected. The controller 8 functions as a liquid feed controller 81, a calculation controller 82, and the like when the CPU executes a program.

The liquid feed controller 81 controls the operations of the excimer lamp 2, the pump 6, and the three-way valve 10 on the basis of the measurement result of the timer 7.

The calculation controller 82 calculates the concentration of total organic carbon (TOC) in sample water on the basis of the detection result of the detector 5.

3. Control Operation by Controller

Figure 4:
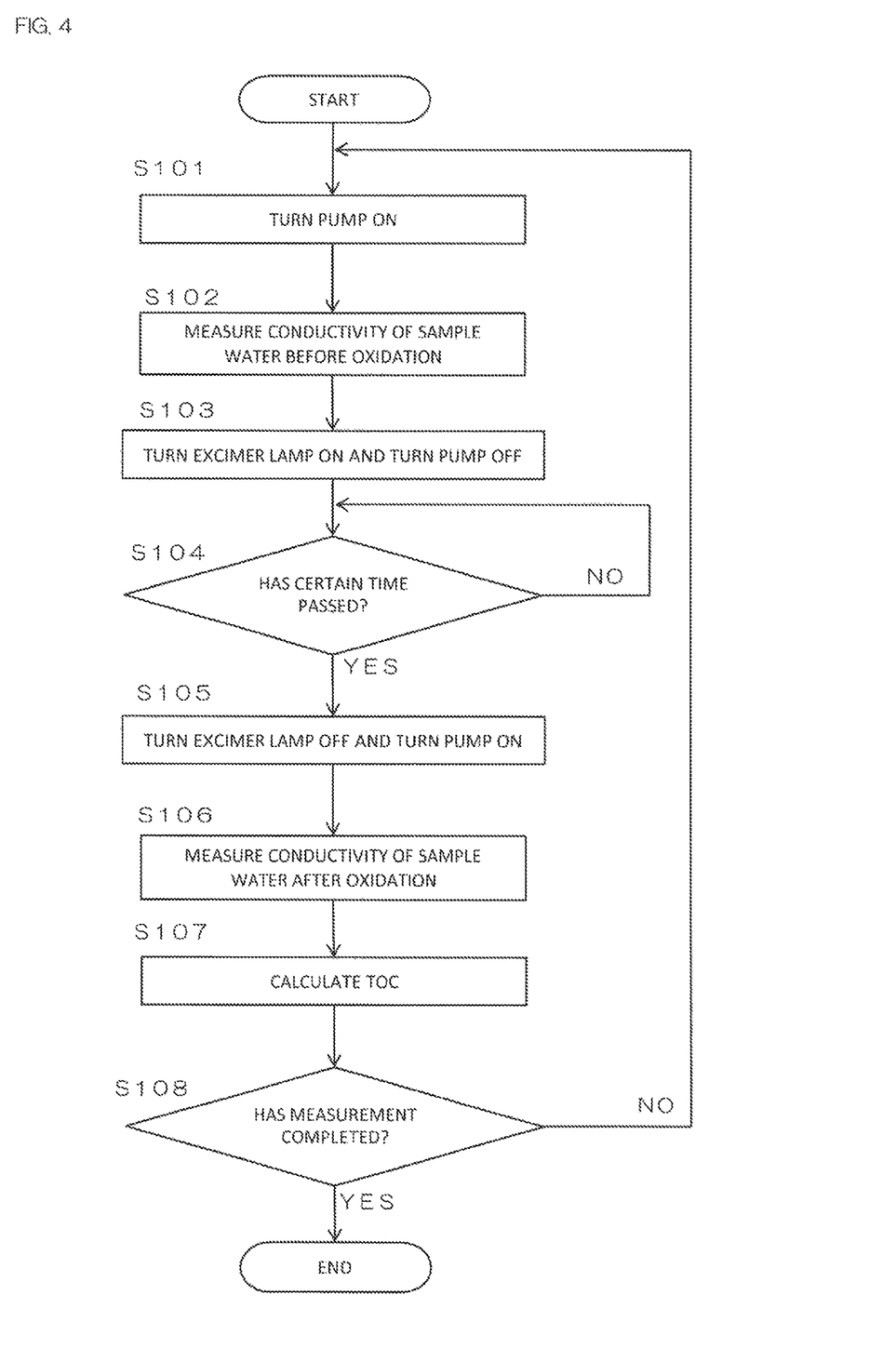
FIG. 4 is a flowchart showing a control operation by the controller.
Figure 5A:
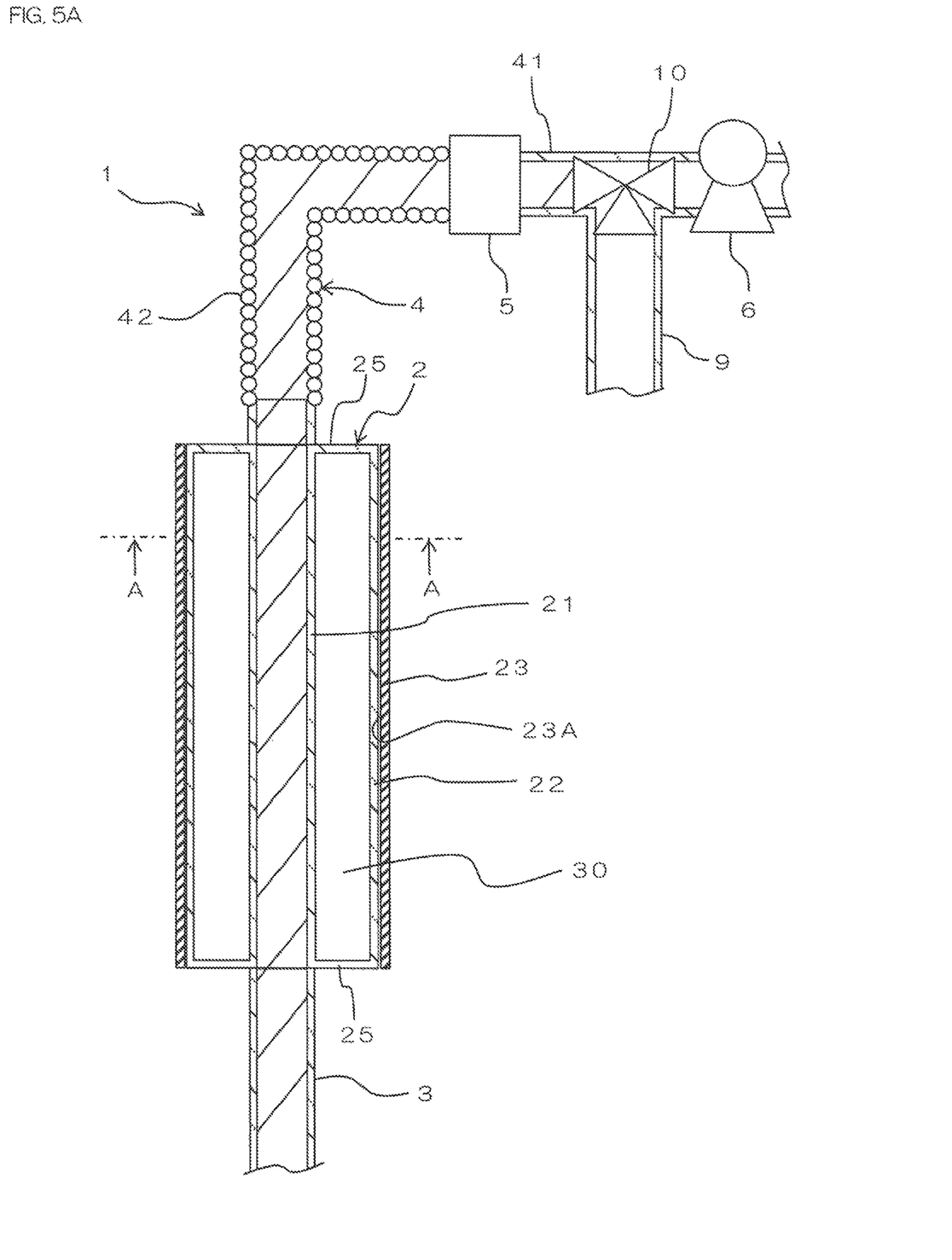
FIG. 5A is a diagram for describing an operation of the water quality measurement device, and is a schematic diagram showing a state in which sample water before oxidation is detected.
Figure 5B:
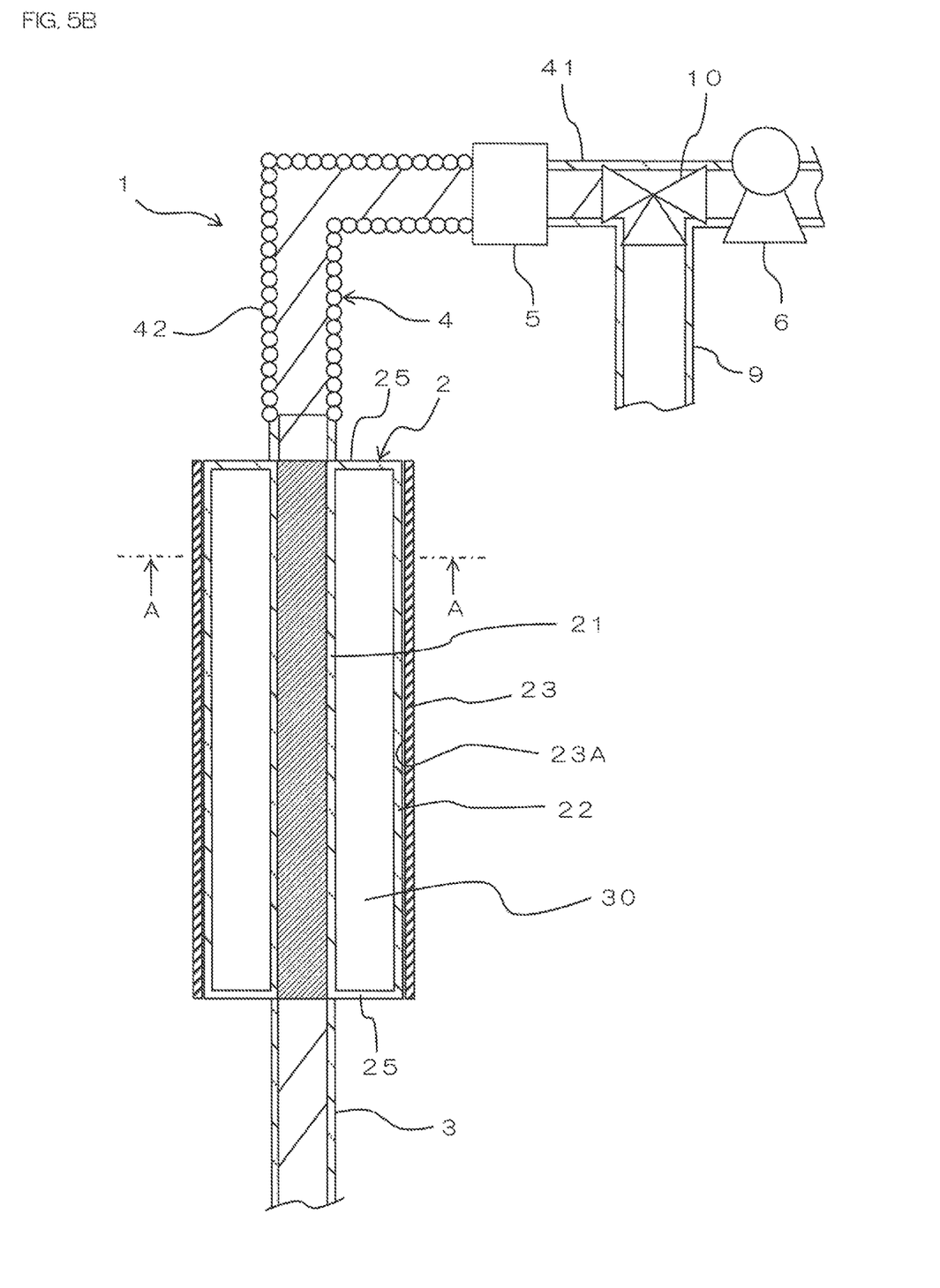
FIG. 5B is a diagram for describing an operation of the water quality measurement device, and is a schematic diagram showing a state in which sample water is oxidized.
Figure 5C:
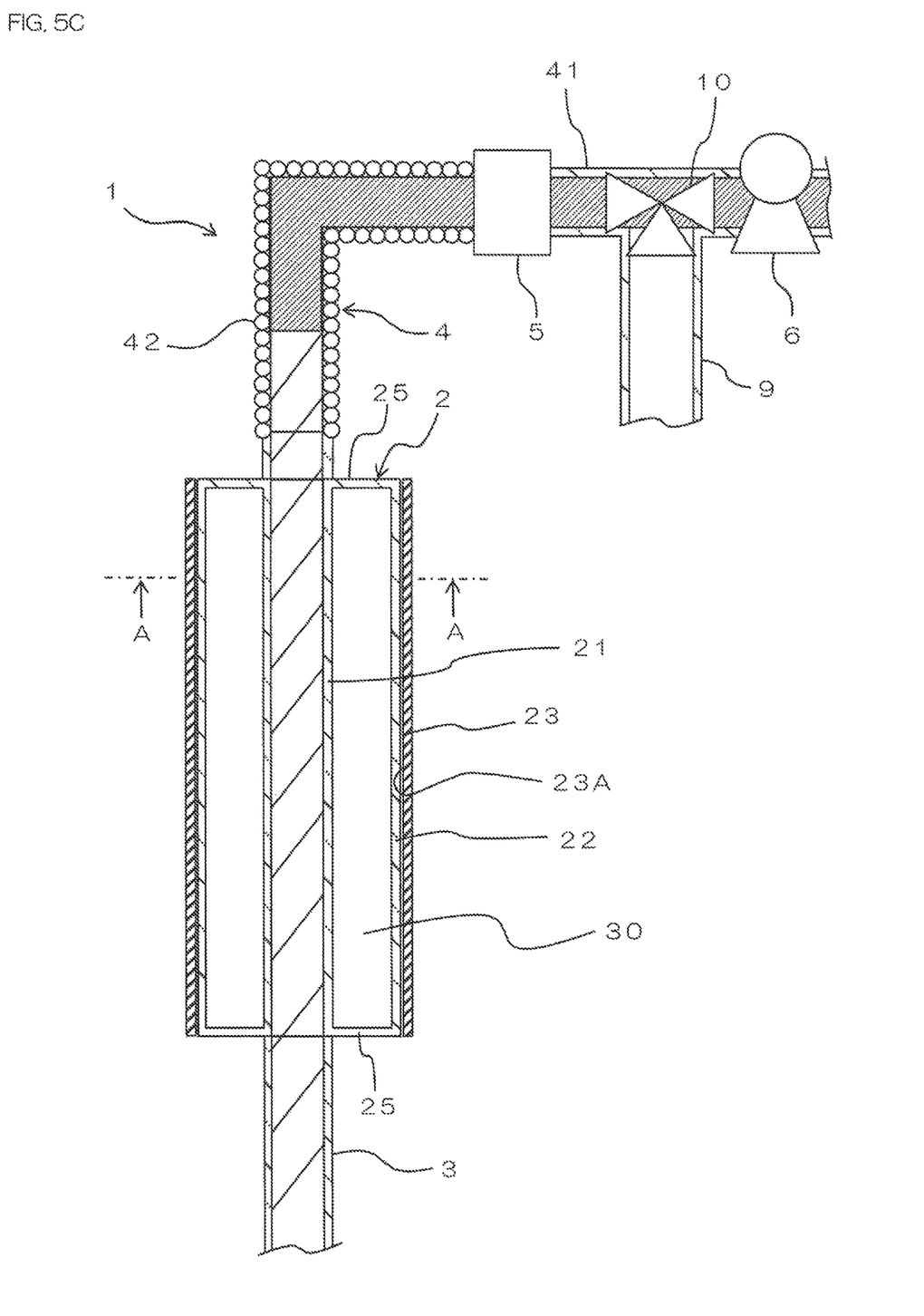
FIG. 5C is a diagram for describing an operation of the water quality measurement device, and is a schematic diagram showing a state in which oxidized sample water is detected.

FIG. 4 is a flowchart showing a control operation by the controller 8. FIGS. 5A to 5C are diagrams for describing operations of the water quality measurement device. Specifically, FIG. 5A is a schematic diagram showing a state in which sample water before oxidation is detected. FIG. 5B is a schematic view showing a state in which sample water is oxidized. FIG. 5C is a schematic diagram showing a state in which oxidized sample water is detected.

In the water quality measurement device 1, when the concentration of total organic carbon (TOC) in sample water is measured, first, operation of the pump 6 is started (pump 6 is turned ON) by the liquid feed controller 81 (Step S101). At this time, the liquid feed controller 81 operates the three-way valve 10, so that the channel from the detector 5 to the pump 6 is opened (so that bypass channel is closed).

Then, as shown in FIG. 5A, the sample water (pure water) flows sequentially into the inflow pipe 3, the inner tube 21 of the excimer lamp 2, and the outflow pipe 4.

At this time, as for the excimer lamp 2, the sample water flows into the inner tube 21 from the one end through the inflow pipe 3 (inflow step). Then, the detector 5 measures the conductivity of the sample water in the outflow pipe 4 (step S102).

Thereafter, when a predetermined time elapses and the time measured by the timer 7 reaches a predetermined value, as shown in FIG. 5B, the liquid feed controller 81 stops the operation of the pump 6 (turns pump 6 OFF) and starts operation of the excimer lamp 2 (turns excimer lamp 2 ON) (step S103).

As a result, the movement of the sample water in the water quality measurement device 1 is stopped, and the excimer lamp 2 irradiates the sample water located in the inner tube 21 with UV light (irradiation step). Then, the sample water in the inner tube 21 of the excimer lamp 2 is oxidized. In the excimer lamp 2, since the inner tube 21 itself is directly used as a channel, it is possible to improve the irradiation efficiency of UV light on sample water. In general, UV light is attenuated by the square of the distance. However, with such a configuration, the distance from the light emission position to sample water can be shortened, and the irradiation efficiency of UV light on sample water can be improved.

Next, when a predetermined time elapses after the start of operation of the excimer lamp 2 and the time measured by the timer 7 (time after start of operation of excimer lamp 2) reaches a predetermined value (YES in step S104), as shown in FIG. 5C, the liquid feed controller 81 stops the operation of the excimer lamp 2 (turns excimer lamp 2 OFF) and starts the operation of the pump 6 (turns pump 6 ON) (step S105).

As a result, sample water (new sample water) flows sequentially into the inflow pipe 3, the inner tube 21 of the excimer lamp 2, and the outflow pipe 4. Then, the sample water oxidized in the inner tube 21 of the excimer lamp 2 is pushed out by the newly introduced sample water, and the pushed out sample water (oxidized sample water) flows into the outflow pipe 4.

Then, the sample water passes through the heat dissipation portion 42 of the outflow pipe 4 and flows into the detector 5. When the sample water passes through the heat dissipation portion 42, the heat of the oxidized sample water is dissipated (heat-dissipated) (heat dissipation step). In addition, the sample water becomes stable when the temperature of the sample water flowing into the detector 5 approaches the ambient temperature. Then, the sample water whose heat is dissipated by the heat dissipation portion 42 flows into the detector 5.

Thus, the sample water oxidized in the inner tube 21 of the excimer lamp 2 is pushed out from the other end of the inner tube 21 when new sample water flows into the water quality measurement device 1 (replaced by new sample water), and flows into the outflow pipe 4 to be sent to the detector 5 (outflow step). Then, the detector 5 measures the conductivity of the sample water (oxidized sample water) in the outflow pipe 4 (step S106: detection step).

Additionally, in the detection step, the conductivity of sample water is detected by the detector 5 while sample water is sent into the outflow pipe 4. For this reason, contamination is reduced and accurate detection can be performed.

Additionally, when the interval before the next measurement is long, the liquid feed controller 81 operates the three-way valve 10, so that the channel from the detector 5 to the pump 6 is closed and the channel from the pipe main body 41 to the bypass pipe 9 (bypass channel) is opened. As a result, pressure from the upstream side causes the sample water to flow into the bypass pipe 9, and the sample water is replaced. Thus, it is possible to curb deterioration of the parts of the water quality measurement device 1.

In the implemented example, the calculation controller 82 calculates the concentration of total organic carbon (TOC) in sample water (step S107), on the basis of the conductivity of the sample water before oxidation measured by the detector 5 (conductivity measured in step S102) and the conductivity of sample water after oxidation measured by the detector 5 (conductivity measured in step S106).

Note that the TOC detection principle of the detector 5 does not necessarily have to be conductivity measurement, and the degradation product of gas-liquid separation may be vaporized and detected by a nondispersive infrared analyzer (NDIR) or the like.

Thereafter, the above-described operation is repeated until the measurement of the sample water in the water quality measurement device 1 is completed. When the measurement of the sample water in the water quality measurement device 1 is completed (YES in step S108), the operations of the excimer lamp 2 and the pump 6 are stopped, and the operation of the water quality measurement device 1 is ended.

4. Measurement Result of Water Quality Measurement Device

Figure 6:
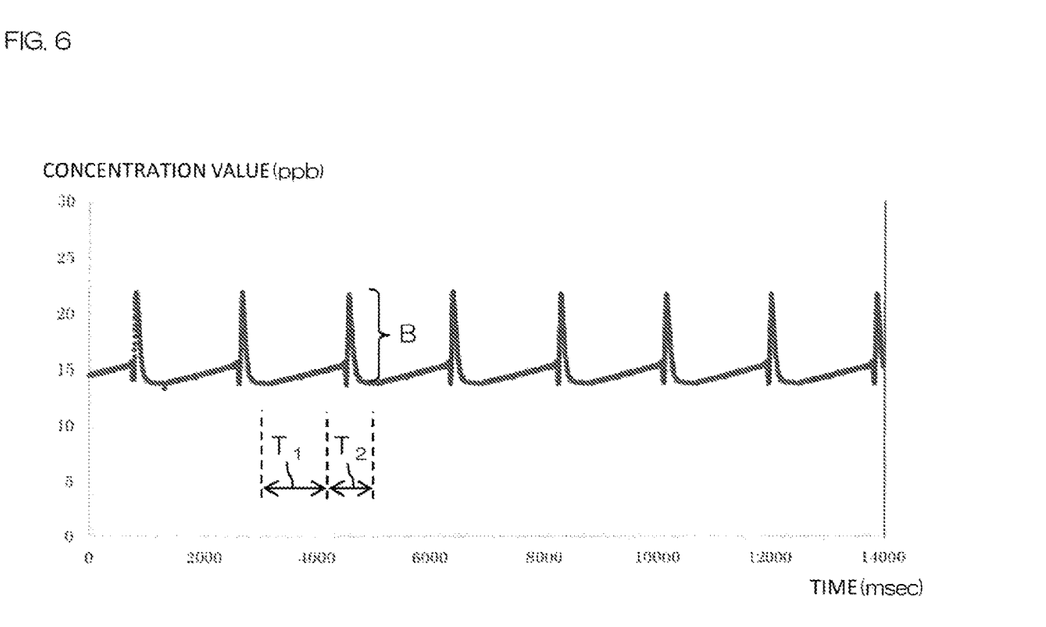
FIG. 6 is a graph showing an example of the result of measurement of the concentration of total organic carbon in sample water by the water quality measurement device.

FIG. 6 is a graph showing an example of the result of measurement of the concentration of total organic carbon in sample water by the water quality measurement device 1.

In FIG. 6, the vertical axis represents the total organic carbon concentration value (ppb), and the horizontal axis represents the elapsed time (msec).

FIG. 6 shows a measurement result when the above-described operation is repeated multiple times in the water quality measurement device 1. In the graph, a concentration value B of total organic carbon is indicated by the difference between the peak and the base of the graph at regular intervals. Additionally, in the graph, in the water quality measurement device 1, the time when sample water is oxidized by the excimer lamp 2 is denoted by $T_1$, and the time when the conductivity is measured by the detector 5 is denoted by $T_2$.

From this graph, as a result of calculating the total organic carbon concentration of the sample water multiple times in the water quality measurement device 1, it can be confirmed that there are few fluctuations (differences) among the multiple concentration values B.

As described above, the water quality measurement device 1 is provided with only one detector 5 that measures conductivity. For this reason, it can be confirmed from the graph of FIG. 6 that the water quality measurement device 1 can give a highly accurate measurement result with less mechanical error as compared with a configuration provided with multiple detectors.

5. Effect (1) According to the embodiment, as shown in FIG. 1, the water quality measurement device 1 includes the twin tube (twin cylinder) excimer lamp 2 as an example of a UV light irradiation portion. The inflow pipe 3 is connected to one end of the inner tube 21 of the excimer lamp 2, and the outflow pipe 4 is connected to the other end of the inner tube 21 of the excimer lamp 2. The detector 5 that measures the conductivity of sample water is interposed in the outflow pipe 4. In the water quality measurement device 1, the degradation product (oxidative degradation product) of sample water is detected. In the water quality measurement device 1, sample water sequentially flows through the inflow pipe 3, the inner tube 21 of the excimer lamp 2, and the outflow pipe 4.

Hence, the channel in the water quality measurement device 1 can be simplified.

Additionally, since the route of sample water is formed of one linear channel, the sample water in the channel is moved so as to be pushed out by the inflow of new sample water.

Hence, the sample water in the channel of the water quality measurement device 1 is allowed to flow out smoothly without remaining.

Additionally, the sample water is oxidized by being irradiated with UV light in the inner tube 21 of the excimer lamp 2. Further, the illuminance of the excimer lamp 2 stabilizes in a shorter time as compared with a mercury lamp or the like.

Hence, it is possible to irradiate the sample water with UV light from the excimer lamp 2 efficiently in a short time.

Furthermore, since the inner tube 21 itself of the excimer lamp 2 is directly used as a channel, the distance from the light emission position to the sample water can be shortened, and the irradiation efficiency of UV light on sample water can be improved.

That is, according to the water quality measurement device 1, the channel of sample water can be simplified, and the irradiation efficiency of UV light on sample water can be improved.

(2) Additionally, according to the embodiment, the detector 5 measures the conductivity of sample water that has flowed into the outflow pipe 4. Then, the degradation product is detected on the basis of the detection result.

Hence, the degradation product can be detected with high accuracy.

(3) Additionally, according to the embodiment, as shown in FIG. 2, in the water quality measurement device 1, the excimer lamp 2 includes the shielding portion 23. The shielding portion 23 covers the outer peripheral surface of the outer tube 22 of the excimer lamp 2.

Hence, it is possible to prevent UV light from leaking from the outer tube 22 to the outside, with a simple configuration in which the outer tube 22 is covered with the shielding portion 23 and other structures are not provided. As a result, the irradiation efficiency of UV light on sample water can be improved.

(4) Additionally, according to the embodiment, as shown in FIG. 1, in the water quality measurement device 1, the outflow pipe 4 includes the heat dissipation portion 42. The heat dissipation portion 42 dissipates the heat of the sample water that has flowed into the outflow pipe 4 (pipe main body 41) (heat dissipation step).

Hence, the heat dissipation portion 42 can dissipate the heat of the oxidized sample water. Then, the degradation product can be detected by the detector 5 with the temperature of the sample water brought close to the ambient temperature.

(5) Additionally, according to the embodiment, as shown in FIG. 2, in the excimer lamp 2 of the water quality measurement device 1, the inner surface 23A of the shielding portion 23 functions as a reflecting surface that reflects UV light.

Hence, the UV light emitted from the excimer lamp 2 and traveling toward the outside can be reflected by the inner surface 23A of the shielding portion 23, and be directed toward the inside of the excimer lamp 2 (inner tube 21). Then, sample water can be oxidized by being irradiated with UV light traveling inward.

As a result, the irradiation efficiency of UV light on sample water can be improved even more.

(6) Additionally, according to the embodiment, the water quality measurement device 1 includes the liquid feed controller 81. The liquid feed controller 81 allows sample water to flow into the inner tube 21 of the excimer lamp 2 from the inflow pipe 3 (inflow step), irradiates the sample water in the inner tube 21 with UV light by the excimer lamp 2 with the inflow of sample water stopped (irradiation step), and resumes the inflow of sample water into the inner tube 21 from the inflow pipe 3 to send the oxidized sample water to the detector 5 through the outflow pipe 4.

Hence, by repeatedly allowing inflow of sample water into the inner tube 21 of the excimer lamp 2 and stopping the inflow, it is possible to repeat the operation of oxidizing sample water by UV light from the excimer lamp 2 and detecting the oxidized sample water by the detector 5.

As a result, the operation of oxidizing sample water and detecting the oxidized sample water by the detector can be performed according to simple control.

In particular, the illuminance of the excimer lamp 2 stabilizes in a short time. Hence, sample water can be detected repeatedly in a short time.

6. Second Embodiment

Hereinafter, a configuration of a water quality measurement device 1 (excimer lamp 2) according to a second embodiment of the present invention will be described with reference to FIG. 7. Note that configurations similar to the first embodiment are assigned similar reference signs, and descriptions are omitted.

Figure 7:
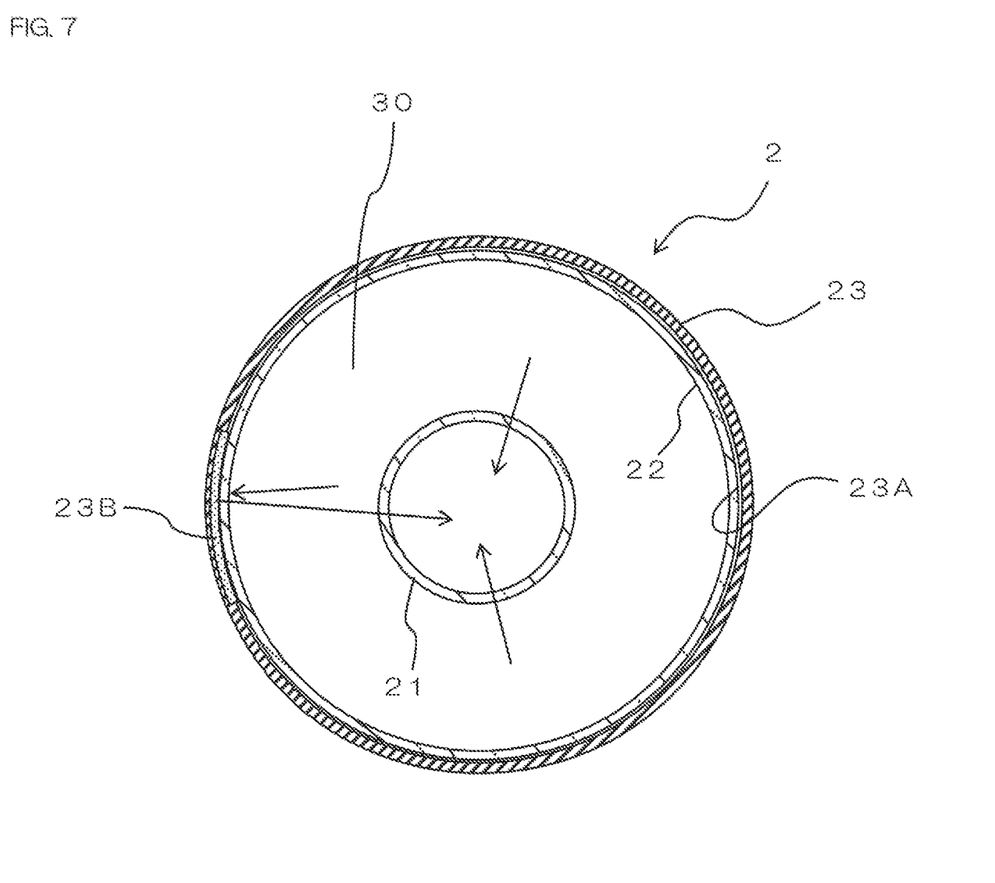
FIG. 7 is a cross-sectional view showing an excimer lamp of a water quality measurement device according to a second embodiment of the present invention.

FIG. 7 is a cross-sectional view showing the excimer lamp 2 of the water quality measurement device 1 according to the second embodiment of the present invention.

The second embodiment is different from the first embodiment described above in that a fluorescent agent 23B is applied to a shielding portion 23 of the excimer lamp 2.

Specifically, in the second embodiment, the fluorescent agent 23B is applied to a part of an inner surface 23A of the shielding portion 23 of the excimer lamp 2.

As a result, when light is emitted from the excimer lamp 2, a part of the light (UV light) is reflected by the fluorescent agent 23B on the inner surface 23A of the shielding portion 23 to be directed radially inward, and flows into an inner tube 21. As a result, light (fluorescence) having a wavelength different from that of the light emitted from the excimer lamp 2 flows into the inner tube 21. Then, the sample water in the inner tube 21 is oxidized by being irradiated with the light beams having different wavelengths.

Thus, in the second embodiment, in the water quality measurement device 1, the fluorescent agent 23B is applied to a part of the inner surface 23A of the shielding portion 23 of the excimer lamp 2.

Accordingly, light (fluorescence) having a wavelength different from the wavelength of UV light emitted from the excimer lamp 2 can be irradiated toward the sample water.

7. Modification

In the above-described embodiment, the water quality measurement device 1 has been described as having only one detector 5. However, in the water quality measurement device 1, the detector 5 may be interposed in each of the inflow pipe 3 and the outflow pipe 4. Then, the conductivity of sample water before oxidation may be measured by the detector 5 interposed in the inflow pipe 3, and the conductivity of sample water after oxidation may be measured by the detector 5 interposed in the outflow pipe 4.

Additionally, in the above-described embodiment, the water quality measurement device 1 has been described as moving the sample water in the channel by the operation of the pump 6. However, the water quality measurement device 1 may be configured such that an adjustable valve is provided instead of the pump 6 and a constant pressure is applied in the channel. In this case, the liquid feed controller 81 moves the sample water in the channel by adjusting the opening of the valve.

Additionally, in the above-described embodiment, the excimer lamp 2 has been described as an example of the UV light irradiation portion. However, a UV light irradiation lamp other than the excimer lamp 2 can be used as the UV light irradiation portion. For example, a UV light irradiation light source may be provided around the passage region through which sample water passes, and UV light may be irradiated inward from around the passage region from the light source toward the sample water. In this case, the UV light irradiation light source may have a shape other than a tubular shape.

DESCRIPTION OF REFERENCE SIGNS 1 water quality measurement device
2 excimer lamp
3 inflow pipe
4 outflow pipe
5 detector
8 controller
21 inner tube 22 outer tube
23 shielding portion
23A inner surface
23B fluorescent agent
81 liquid feed controller

The invention claimed is:

1. A water quality measurement device comprising:
a UV light irradiation portion that has a passage region through which sample water passes and irradiates the sample water with UV light from around the passage region;
an inflow pipe that is arranged to allow sample water to flow into the passage region;
an outflow pipe that is arranged to allow the sample water, which has been oxidized by being irradiated with UV light by the UV light irradiation portion, to flow out of the passage region, the outflow pipe being located downstream of the passage region;
a heat dissipation portion that dissipates heat of the sample water, the heat dissipation portion being provided on the outflow pipe; and
a detector that detects a degradation product that has flowed out into the outflow pipe, the detector being located downstream of the heat dissipation portion, wherein:
the UV light irradiation portion is a twin tube excimer lamp that has an inner tube in which an internal space is formed as the passage region and an outer tube disposed around the inner tube, and emits UV light by generating a discharge between electrodes provided on an inner peripheral surface of the inner tube and an outer peripheral surface of the outer tube;
the inflow pipe is arranged to allow sample water to flow into the inner tube from one end;
the outflow pipe is arranged to allow the sample water oxidized by being irradiated with UV light in the inner tube to flow out from the other end of the inner tube;
the water quality measurement device further comprises a liquid feed controller that is arranged to repeat an operation of allowing sample water to flow into the inner tube from the inflow pipe, irradiating the sample water in the inner tube with UV light by the excimer lamp with the inflow of sample water stopped to oxidize the sample water, and resuming the inflow of sample water into the inner tube from the inflow pipe to send the oxidized sample water to the detector through the outflow pipe;
the liquid feed controller is arranged to stop the operation of the excimer lamp after sample water in the inner tube has been irradiated with UV light by the excimer lamp and to start the operation of the excimer lamp after the sample water irradiated with the UV light has exited the inner tube; and
the heat dissipation portion dissipates the heat of sample water that has been oxidized by being irradiated with UV light and that flows out of the inner tube into the outflow pipe, allowing the dissipated sample water to flow into the detector.

2. The water quality measurement device according to claim 1, wherein the detector detects the degradation product by measuring conductivity of the sample water that has flowed into the outflow pipe.

3. The water quality measurement device according to claim 1, wherein the excimer lamp includes a shielding portion that covers an outer peripheral surface of the outer tube and prevents UV light from leaking to the outside.

4. The water quality measurement device according to claim 3, wherein a reflecting surface that reflects UV light is formed on an inner surface of the shielding portion.

5. The water quality measurement device according to claim 3, wherein a fluorescent agent is applied to an inner surface of the shielding portion.

6. A water quality measurement method comprising:
an inflow step of allowing sample water to flow, through an inflow pipe, into a passage region of a UV light irradiation portion that has the passage region through which sample water passes and irradiates the sample water with UV light from around the passage region;
an irradiation step of irradiating the sample water in the passage region with UV light by the UV light irradiation portion;
an outflow step of allowing the sample water, which has been oxidized by being irradiated with UV light by the UV light irradiation portion, to flow into an outflow pipe from the passage region, the outflow pipe being located downstream of the passage region;
a heat dissipation step of dissipating heat of the sample water at a location at a heat dissipation region of the outflow pipe, downstream from the passage region, and
a detection step of detecting a degradation product that has flowed into the outflow pipe by a detector, the detector being located downstream of the heat dissipation region of the outflow pipe, wherein:
in the inflow step, sample water is allowed to flow, through the inflow pipe, from a first end into an inner tube of a twin tube excimer lamp that has the inner tube in which an internal space is formed as the passage region and an outer tube disposed around the inner tube, and emits UV light by generating a discharge between electrodes provided on an inner peripheral surface of the inner tube and an outer peripheral surface of the outer tube;
in the irradiation step, the sample water in the inner tube is irradiated with UV light by the excimer lamp;
in the outflow step, the sample water oxidized by being irradiated with UV light in the inner tube is allowed to flow into the outflow pipe from the othera second end of the inner tube opposite the first end;
an operation of allowing sample water to flow into the inner tube from the inflow pipe, irradiating the sample water in the inner tube with UV light by the excimer lamp with the inflow of sample water stopped, and resuming the inflow of sample water into the inner tube from the inflow pipe to send the oxidized sample water to the detector through the outflow pipe is repeated;
stopping the excimer lamp from operating after the sample water in the inner tube i-s-has been irradiated with UV light by the excimer lamp, and starting the operation of the excimer lamp after the sample water irradiated with the UV light has exited the inner tube; and
allowing sample water that has been oxidized by being irradiated with UV light, that has been heat-dissipated, and that flows out of the inner tube into the outflow pipe to flow to the detector.

7. The water quality measurement method according to claim 6, wherein, in the detection step, the degradation product is detected by measuring conductivity of the sample water that has flowed into the outflow pipe.

8. The water quality measurement device according to claim 1, wherein the liquid feed controller is arranged to stop the operation of the excimer lamp when a predetermined time elapses after starting the operation of the excimer lamp.

9. The water quality measurement method according to claim 6, wherein the operation of the excimer lamp is stopped when a predetermined time elapses after starting the operation of the excimer lamp.

* * * * *